(12) United States Patent
Kobayashi

(10) Patent No.: US 10,417,757 B2
(45) Date of Patent: Sep. 17, 2019

(54) IMAGE INSPECTION APPARATUS AND IMAGE INSPECTION METHOD

(71) Applicant: DAIHEN Corporation, Osaka-shi, Osaka (JP)

(72) Inventor: Takumi Kobayashi, Osaka (JP)

(73) Assignee: DAIHEN Corporation, Osaka (JP)

( * ) Notice: Subject to any disclaimer, the term of this patent is extended or adjusted under 35 U.S.C. 154(b) by 176 days.

(21) Appl. No.: 14/637,938

(22) Filed: Mar. 4, 2015

(65) Prior Publication Data

US 2015/0254827 A1   Sep. 10, 2015

(30) Foreign Application Priority Data

Mar. 7, 2014  (JP) .................................. 2014-045231

(51) Int. Cl.
| | |
|---|---|
| *G06T 7/00* | (2017.01) |
| *G06T 5/30* | (2006.01) |
| *G01N 21/956* | (2006.01) |
| *G06T 7/254* | (2017.01) |
| *G01N 21/95* | (2006.01) |

(52) U.S. Cl.
CPC ....... *G06T 7/001* (2013.01); *G01N 21/95607* (2013.01); *G06T 5/30* (2013.01); *G06T 7/254* (2017.01); *G01N 2021/9513* (2013.01); *G01N 2021/95638* (2013.01); *G06T 2207/30148* (2013.01)

(58) Field of Classification Search
None
See application file for complete search history.

(56) References Cited

U.S. PATENT DOCUMENTS

| | | | | |
|---|---|---|---|---|
| 5,537,669 | A  * | 7/1996 | Evans ................... | G03F 7/7065 382/141 |
| 7,085,379 | B1 * | 8/2006 | Kagechi ................ | H04N 19/00 375/E7.026 |
| 2001/0033683 | A1 * | 10/2001 | Tanaka .................... | G06T 7/001 382/149 |
| 2005/0259245 | A1 * | 11/2005 | Cemic ................ | G01N 21/8806 356/237.2 |

(Continued)

FOREIGN PATENT DOCUMENTS

| | | |
|---|---|---|
| JP | 2001-343337 | 12/2001 |
| JP | 2012-194030 | 10/2012 |

*Primary Examiner* — Edemio Navas, Jr.
(74) *Attorney, Agent, or Firm* — Hamre, Schumann, Mueller & Larson, P.C.

(57) ABSTRACT

An image inspection apparatus is provided with an image sensing unit, a determination unit, and a reference image generation unit. The image sensing unit captures an inspection target. The determination unit takes a difference between a reference image that includes a solid image of the inspection target and a captured image that is captured of the inspection target. The determination unit thereby extracts an image that is not included in an image of the inspection target in the reference image, and determines the quality of the inspection target based on the extracted image. The reference image generation unit generates the reference image that is used by the determination unit by performing predetermined image processing to change to an image showing the inspection target that is included in the captured image into a solid image.

11 Claims, 9 Drawing Sheets

(56) References Cited

U.S. PATENT DOCUMENTS

| | | | | |
|---|---|---|---|---|
| 2006/0093235 A1* | 5/2006 | Takarada | ............... | G06T 5/002 382/264 |
| 2007/0031026 A1* | 2/2007 | Kurihara | ............... | G06T 7/001 382/149 |
| 2007/0286515 A1* | 12/2007 | Kim | ............... | H04N 19/117 382/254 |
| 2009/0196489 A1* | 8/2009 | Le | ............... | G01N 21/9503 382/148 |
| 2012/0026316 A1* | 2/2012 | Nagahama | ............... | G01N 21/95607 348/92 |
| 2012/0307236 A1* | 12/2012 | Ortner | ............... | G01N 21/9505 356/239.3 |
| 2013/0182941 A1* | 7/2013 | Hikida | ............... | G06T 7/0004 382/149 |
| 2014/0101485 A1* | 4/2014 | Wegener | ............... | H03M 7/3068 714/32 |

* cited by examiner

Binarization

Enlargement processing

Reduction processing

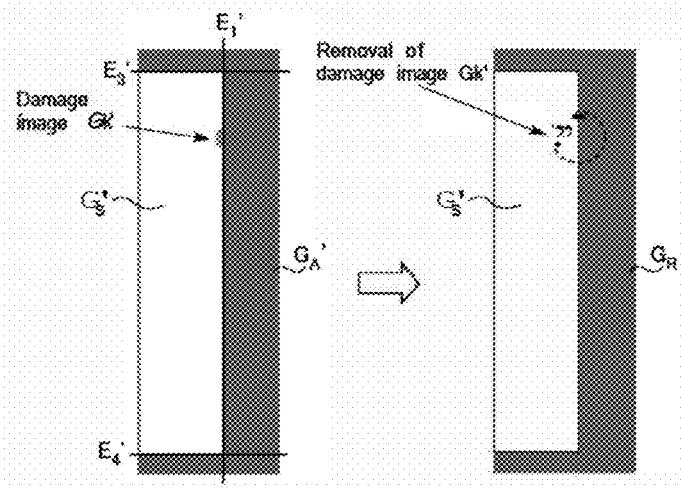
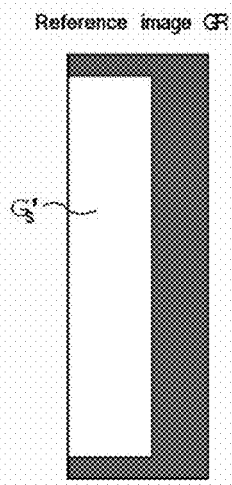 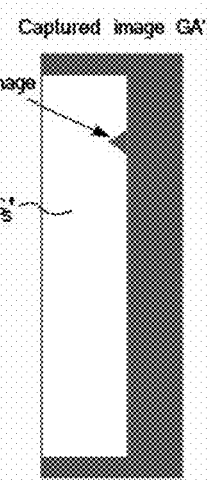 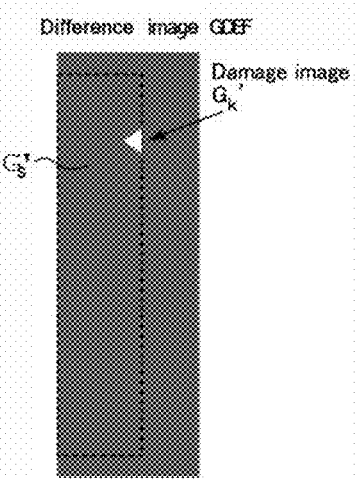

FIG. 13A
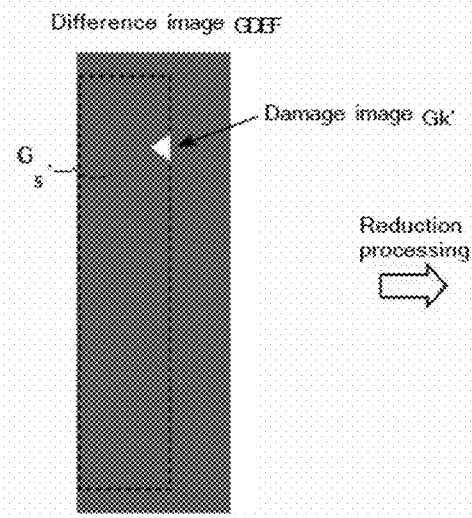
FIG. 13B
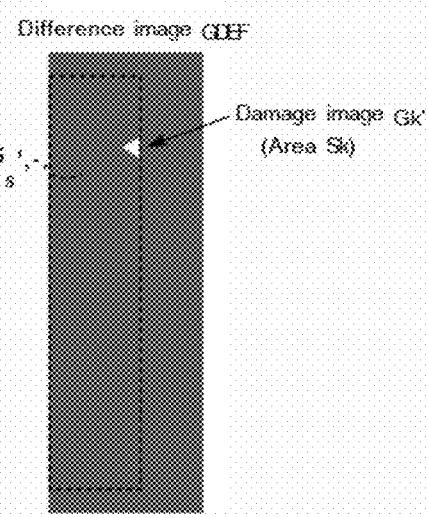
FIG. 14 - PRIOR ART
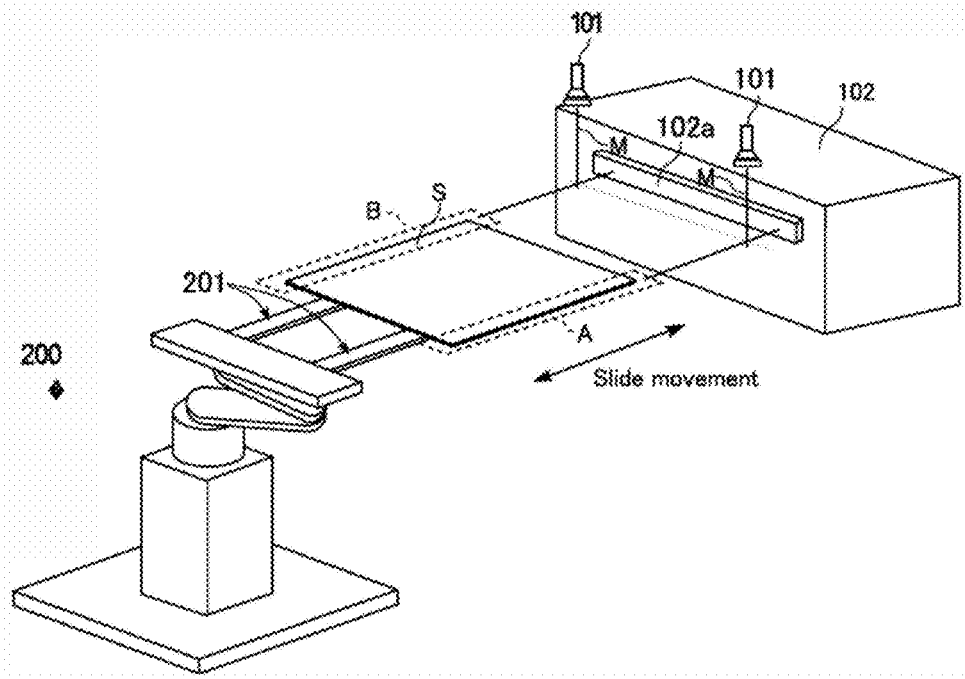

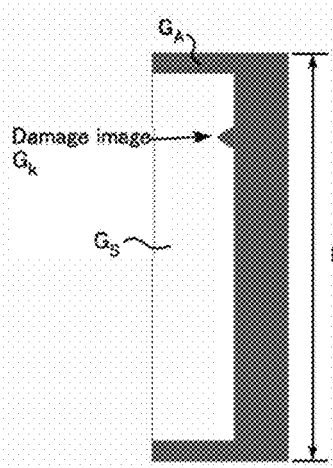
FIG. 15A - PRIOR ART
Standard image
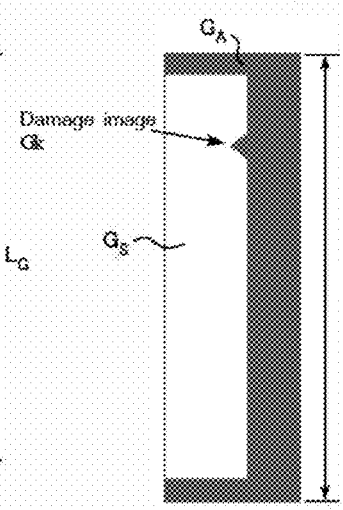
FIG. 15B - PRIOR ART
Image in case of slow movement speed
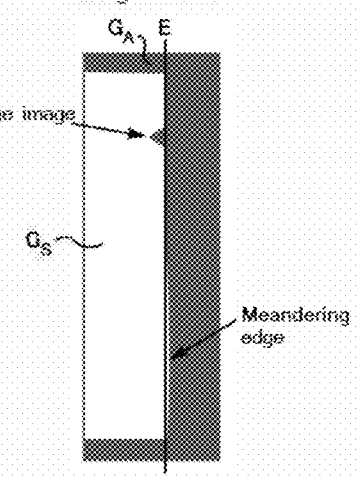
FIG. 15C - PRIOR ART
Image in case of swinging left & right during movement

IMAGE INSPECTION APPARATUS AND IMAGE INSPECTION METHOD

BACKGROUND OF THE INVENTION

1. Field of the Invention

The present invention relates to an image inspection apparatus and an image inspection method that capture an inspection target with a camera and inspect the inspection target for damage using the captured image. In particular, the present invention relates to an image inspection apparatus and an image inspection method that are suitable for inspecting a substrate (liquid crystal substrate, etc.) for damage while the substrate is being conveyed by a handling robot.

2. Description of Related Art

Conventionally, image inspection methods that capture an inspection target with a camera and inspect the inspection target for damage using the captured image are known.

For example, JP-A-2001-343337 discloses a method that uses a camera to capture a printed circuit board to be inspected (hereinafter, "inspection target substrate"), and inspects the inspection target substrate for defects using the captured image. Also, JP-A-2012-194030 discloses a method that detects for flaws in an inspection target substrate by capturing the inspection target substrate with a camera, comparing the captured image with a reference image acquired in advance (image that is captured of a printed circuit board without flaws), and extracting an image of a flawed portion of the inspection target substrate from data of the difference between both images.

In a substrate processing system that uses a substrate handling robot to convey substrates such as liquid crystal substrates in order to processing chambers for performing multiple processes and performs a predetermined process in each processing chamber, side portions of the substrates may suffer cracks, breaks or other damage due to occurrences such as the substrates coming in contact with the processing chambers while being conveyed by the substrate handling robot. When a substrate suffers damage, the substrate becomes defective and thus needs to be quickly discharged from the substrate processing system.

Application of a conventional substrate inspection method using pattern matching to a substrate processing system requires that each inspection area of a substrate that is not damaged be captured with a camera in advance and that reference images be prepared, and thus there is a problem in that the workload involved is considerable.

For example, in the case where, as shown in FIG. 14, a configuration is adopted in which a camera 101 using a line sensor is disposed on both sides of a substrate entrance 102a of a processing chamber 102, and both sides of a substrate S in a width direction are captured when a substrate handling robot 200 takes the substrate S in and out the processing chamber 102 to acquire images of a right area A and a left area B, the orientation of the substrate S and the movement speed and movement direction of a hand 201 change slightly every time the substrate handling robot 200 conveys the substrate S, and thus the shapes of substrate images $G_S$ showing the substrate S in captured images $G_A$ that are captured of the right area A, for example, are all different, as shown in FIGS. 15A-C.

Note that FIG. 15A shows a standard captured image $G_A$, FIG. 15B shows the captured image $G_A$ in the case where the hand 201 moves slowly, and FIG. 15C shows the captured image $G_A$ in the case where the hand 201 meanders in comparison with FIG. 15A. In FIG. 15B, a length $L_G$ in a lengthwise direction of the captured image $G_A$ is longer than in FIG. 15A. The length in the lengthwise direction of a damage image $G_k$ showing a damaged portion of the substrate S is thus also longer in FIG. 15B than in FIG. 15A. In FIG. 15C, a right-side edge E of the captured image $G_A$ has a portion that meanders rather than being straight.

Accordingly, in the case of comparing each captured image $G_A$ with a reference image $G_R$, processing for aligning the images of the substrate S in both the images $G_A$ and $G_R$ will be troublesome. In particular, since the shape and size of the substrate image $G_S$ in the captured image $G_A$ differs from the shape and size of the substrate image $G_S$ in the reference image $G_R$ in the case where the movement speed or movement direction of the hand 201 varies, an inconvenience occurs in that the damage image $G_k$ cannot be correctly extracted by pattern matching. To avoid this inconvenience, it is conceivable to acquire multiple reference images $G_R$ under different conveyance conditions of the substrate S. However, there are problems with this method, including the increased time and effort involved in acquiring the reference images $G_R$, a larger memory capacity for the reference images $G_R$, and more troublesome processing for selecting, for each captured image $G_A$, a reference image $G_R$ to be used in pattern matching that corresponds to the captured image $G_A$. Similar problems arise in the case of the captured image $G_B$ that is captured of the left area B.

SUMMARY OF THE INVENTION

The present invention was made in view of the above problems. As such, an object of the present invention is to provide an image inspection apparatus and an image inspection method that are able to create a reference image from a captured image of an inspection target, and inspect the quality of the inspection target by pattern matching using both images.

An image inspection apparatus according to a first aspect of the present invention is provided with an image sensing unit for capturing an inspection target to acquire a captured image, a reference image generation unit for generating a reference image that includes a solid image of the inspection target, by performing predetermined image processing on an image portion of the inspection target that is included in the captured image, and a determination unit for extracting an image that is not included in the reference image to generate an extracted image by taking a difference between the reference image and the captured image, and determining a quality of the inspection target based on the extracted image.

Preferably, the image processing that is performed by the reference image generation unit is closing processing on an image of the inspection target that is included in the captured image.

Preferably, the inspection target is a rectangular substrate that has two side portions spaced from each other and that is conveyed by a handling robot. Preferably, the image sensing unit includes a pair of cameras that capture the two side portions of the substrate. Preferably, each of the cameras has a line sensor extending in a direction orthogonal to a conveyance direction of the substrate by the handling robot. Preferably, an image of one of the two side portions of the substrate is taken by an image capture operation being performed during a period in which the line sensor moves relative to the one side portion of the substrate as a result of the substrate being conveyed by the handling robot.

Preferably, the reference image generation unit, after performing the closing processing, further detects a pseudo edge that is equivalent to an outline of the substrate in the captured image. Preferably, the reference image generation unit generates the reference image based on an image area surrounded by the pseudo edge.

Preferably, the determination unit performs reduction processing on the extracted image, and, in a case where an area of an image resulting from the reduction processing is greater than or equal to a preset threshold, determines that the inspection target is defective.

An image inspection method according to a second aspect of the present invention is provided with a first step of capturing an inspection target with an image sensing unit to acquire a captured image, a second step of generating a reference image that includes a solid image of the inspection target, by performing predetermined image processing on an image portion of the inspection target that is included in the captured image, and a third step of generating an extracted image obtained through extracting an image that is not included in the reference image by taking a difference between the reference image and the captured image, and determining a quality of the inspection target based on the extracted image.

Preferably, the inspection target is a rectangular substrate that has two side portions spaced from each other and that is conveyed by a handling robot. Preferably, the image sensing unit includes a pair of cameras that capture the two side portions of the substrate. Preferably, each of the cameras has a line sensor extending in a direction orthogonal to a conveyance direction of the substrate by the handling robot. Preferably, in the first step, an image of one of the two side portions of the substrate is taken by an image capture operation being performing during a period in which the line sensor moves relative to the one side portion of the substrate as a result of the substrate being conveyed by the handling robot. Preferably, in the second process, the reference image is generated by performing closing processing on an image of the inspection target that is included in the image taken with each camera.

According to the present invention, a reference image is generated from a captured image that is captured of an inspection target with an image sensing unit. Accordingly, the time and effort involved in acquiring a reference image in advance is no longer necessary. Memory for storing the reference image also is no longer necessary.

Also, according to the present invention, image capture of the inspection target (e.g., rectangular substrate) may be performed during the period in which the inspection target is being conveyed with the handling robot. In this case, the quality of an inspection target is inspected using a captured image of the inspection target, thus enabling the quality of the inspection target to be appropriately determined, even in the case where the conveyance speed of the handling robot varies or variation occurs in the placement position of the inspection target on the handling robot. That is, because the reference image is generated from a captured image of the inspection target, the shape of the substrate portion in the captured image will be substantially the same as the shape of the substrate portion in the reference image. Therefore, the two images of the substrate portions can be easily aligned when taking the difference between the captured image and the reference image. Accordingly, a damage image can be accurately detected from the difference image, and the quality of the inspection target can be determined with high accuracy.

BRIEF DESCRIPTION OF THE DRAWINGS

FIGS. 11A and 11B are diagrams for illustrating processing for generating a reference image.

FIGS. 12A-C are diagrams for illustrating processing for generating a difference image of a reference image and a captured image.

FIGS. 13A and 13B are diagrams for illustrating processing for extracting a damage image.

FIG. 14 is a diagram showing a configuration that detects damage to a substrate when the substrate is loaded into a processing chamber by a substrate handling robot.

FIGS. 15A-C are diagrams showing examples of captured images in the case where the image capture conditions of the substrate S differ.

DESCRIPTION OF THE PREFERRED EMBODIMENTS

Preferred embodiments of the present invention will be specifically described with reference to the accompanying drawings, taking an image inspection apparatus that is applied to a substrate processing system as an example.

Figure 1:
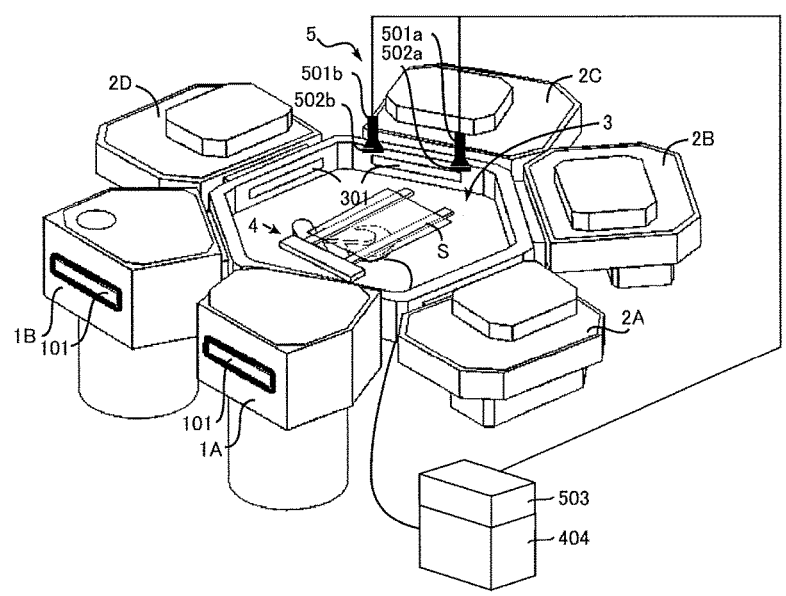
FIG. 1 is a perspective view showing an example of a substrate processing system to which an image inspection apparatus according to the present invention is applied.
Figure 2:
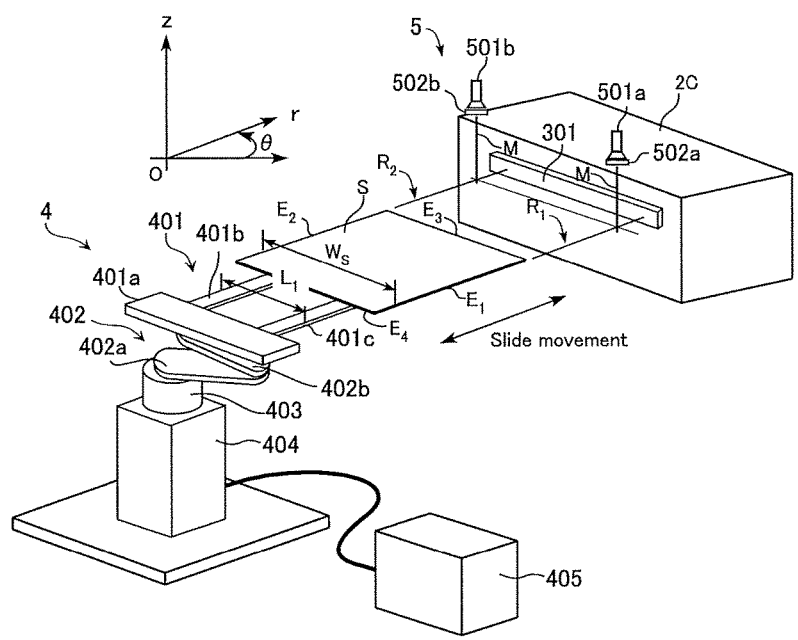
FIG. 2 is a perspective view showing a configuration of a substrate handling robot.

FIG. 1 is a perspective view showing an example of a substrate processing system to which an image inspection apparatus according to the present invention is applied. FIG. 2 is a perspective view showing a configuration of a substrate handling robot 4.

A substrate processing system X shown in FIG. 1 is configured to include two load lock chambers 1 (1A, 1B), four processing chambers 2 (2A, 2B, 2C, 2D), one conveyance chamber 3, one substrate handling robot 4, and an image inspection apparatus 5. The two load lock chambers 1A and 1B and the four processing chambers 2A, 2B, 2C and 2D are disposed around the conveyance chamber 3. The conveyance chamber 3 is hexagonal in plan view, with the load lock chambers 1A and 1B being disposed at two adjoining sides, and the processing chambers 2A, 2B, 2C and 2D being disposed at the remaining four sides. Also, the substrate handling robot 4 is disposed in the center of the conveyance chamber 3. A horizontally long rectangular window 301 for taking the substrate S in and out using the substrate handling robot 4 is formed at a predetermined height in each lateral surface of the conveyance chamber 3.

The processing chambers 2 are chambers that perform predetermined manufacturing process processing on the surface of a substrate S such as a liquid crystal substrate or a semiconductor substrate. The manufacturing process processing is, for example, processing such as thin film formation processing using CVD (Chemical Vapor Deposition) technology or PVD (Physical Vapor Deposition) technology, circuit pattern formation processing using dry etching technology or lithography technology, substrate planarization processing using CMP (Chemical Mechanical Polishing) technology, substrate cleaning processing using dry cleaning technology, and junction formation processing using ion implantation technology.

The load lock chambers 1 are chambers for loading the substrate S into the conveyance chamber 3 from outside the substrate processing system X and discharging the substrate S to outside the substrate processing system X while maintaining a vacuum state in the conveyance chamber 3. In the present embodiment, the load lock chamber 1A is a chamber for loading the substrate S and the load lock chamber 1B is a chamber for discharging the substrate S.

Although not shown, an interface for loading the substrate S into the substrate processing system X and discharging the substrate S from the substrate processing system X is provided on the outer side of the load lock chambers 1A and 1B. A horizontally long rectangular window 101 for taking the substrate S in and out of the interface is provided in the outer lateral surface of the load lock chambers 1A and 1B.

The interface includes a substrate handling robot and one or more cassettes in which a plurality of substrates S are housed, and functions to remove substrates S from the cassettes and convey the substrates S into the substrate processing system X through the window 101 of the load lock chamber 1A using the substrate handling robot, and to receive processed substrates S through the window 101 of the load lock chamber 1B and house the processed substrates S in the cassettes using the substrate handling robot. Note that the cassettes are conveyed to the interface of the substrate processing system X from another location by a self-propelled vehicle.

After receiving a substrate S that has been loaded into the load lock chamber 1A and conveying the substrate S in order to the four processing chambers 2A, 2B, 2C and 2D, the substrate handling robot 4 discharges the processed substrate S to the load lock chamber 1B.

The substrate handling robot 4 is, as shown in FIG. 2, an articulated robot that has a hand 401 for carrying substrates S and that displaces the position of the hand 401 using an articulated arm. Also, the substrate handling robot 4 is a cylindrical coordinate robot that controls the position of the hand 401 using cylindrical coordinates. The substrate handling robot 4, as a mechanism for controlling the position of the hand 401, is provided with a horizontal actuator 402 that performs horizontal movement (movement along an r axis in cylindrical coordinates) of the hand 401, a rotational actuator 403 that performs rotational movement (movement along an θ axis in cylindrical coordinates) of the hand 401 by rotating the horizontal actuator 402, a lifting actuator 404 that performs lifting and lowering movement (movement along a z axis in cylindrical coordinates) of the hand 401 by moving the rotational actuator 403 up and down, and a robot controller 405 that controls the operations of the horizontal actuator 402, the rotational actuator 403, and the lifting actuator 404.

The lifting actuator 404 of the substrate handling robot 4 includes a shaft that is movable up and down and supports the rotational actuator 403 and a motor (not visible in FIG. 2) coupled to the shaft, and the shaft is moved up and down by the torque of the motor. The rotational actuator 403 of the substrate handling robot 4 includes a motor disposed with a rotor facing vertically, and the horizontal actuator 402 is directly coupled to a tip portion of the rotor.

The motor of the lifting actuator 404 and the motor of the rotational actuator 403 are constituted by AC servo motors, and the robot controller 405 controls the position of the hand 401 along the z axis by controlling the revolutions of the AC servo motor of the lifting actuator 404, and controls the position of the hand 401 along the θ axis by controlling the revolutions of the AC servo motor of the rotational actuator 403. Note that the cylindrical coordinates (r, θ, z) are set in the substrate handling robot 4 in a virtual manner with a position at which the axis of the shaft of the lifting actuator 404 intersects a horizontal line passing through the center of the window 101 of the load lock chamber 1A as an origin O (0, 0, 0), for example.

The hand 401 has a structure in which a pair of arms 401b and 401c consisting of vertically long high-stiffness plate material are fixed to one long side of a horizontally long support plate 401a, as shown in FIG. 2. The pair of arms 401b and 401c are fixed to positions that are symmetrical about the center of the support plate 401a in the longitudinal direction, and the longitudinal direction of the arms 401b and 401c and the longitudinal direction of the support plate 401a are orthogonal to each other.

The hand 401 holds the rectangular substrate S by supporting both ends of the substrate S in the width direction from below with the two arms 401b and 401c. Accordingly, the upper surface of tip portions of the arms 401b and 401c serves as a substrate placement portion on which the substrate S is placed. A distance $L_1$ between the arm 401b and the arm 401c is set to be slightly shorter than a size $W_S$ of the substrate S in the width direction.

The horizontal actuator 402 is constituted by links coupled such that the pair of arms 402a and 402b are rotatable, and the hand 401 is attached to the tip of the arm 402b. The substrate handling robot 4, by placing the substrate S on the substrate placement portion with the hand 401 held horizontally, and then lifting and lowering the hand 401, rotating the hand 401 in a horizontal plane and moving the hand 401 straight ahead in this state, receives the substrate S from the load lock chamber 1A and sets the substrate S in the processing chambers 2A, 2B, 2C and 2D in order.

The image inspection apparatus 5 includes two cameras 501a and 501b, two lights 502a and 502b, and an image inspection controller 503. When housing the substrate Sin the processing chamber 2, the substrate handling robot 4, as shown in FIG. 2, extends the arms 402a and 402b of the horizontal actuator 402 and moves the substrate S placed on the hand 401 horizontally into the processing chamber 2, with the hand 401 directly opposite the window 301 of the conveyance chamber 3 that leads to the processing chamber 2. The two cameras 501a and 501b are disposed in predetermined positions above movement loci $R_1$ and $R_2$ of right and left edges $E_1$ and $E_2$ when the substrate S moves horizontally (positions near the window 301 that leads to the processing chamber 2 in FIGS. 1 and 2), such that respective optical axes M of the cameras 501a and 501b point toward the movement loci $R_1$ and $R_2$.

Figure 3:
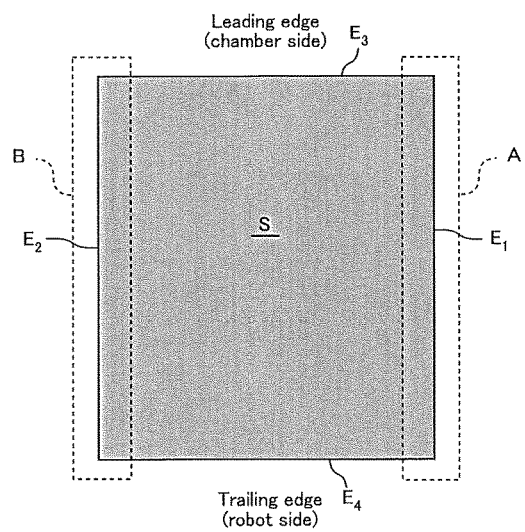
FIG. 3 is a diagram showing areas of a substrate that are captured with a camera.

The cameras 501a and 501b are line cameras that use a monochrome line sensor as the image sensor. The camera 501a is oriented such that the array direction of the pixels of the line sensor is orthogonal to the movement locus $R_1$. Similarly, the camera 501b is oriented such that the array direction of the pixels of the line sensor is orthogonal to the movement locus $R_2$. The cameras 501a and 501b take images $G_A$ and $G_B$ of areas A and B on right and left side portions of the substrate S, as shown in FIG. 3 by, for example, starting image capture at the timing at which a leading edge $E_3$ of the substrate S enters the field of view of the cameras 501a and 501b when the substrate S is housed in the processing chamber 2, and stopping image capture at the timing at which a trailing edge $E_4$ of the substrate S leaves the field of view of the cameras 501a and 501b.

Note that the captured images $G_A$ and $G_B$ are taken when the substrate S is removed from the processing chamber 2. That is, the captured images $G_A$ and $G_B$ are captured while the cameras 501a and 501b are moving relative to the areas A and B, as a result of the horizontal movement of the substrate S when the substrate S is taken in and out of the processing chamber 2 by the substrate handling robot 4.

In the present embodiment, the cameras 501a and 501b are disposed so as to capture the areas A and B of the substrate S when the substrate S is taken in and out of the processing chamber 2C, but the cameras 501a and 501b may be disposed so as to capture the areas A and B of the substrate S when the substrate S is taken in and out of a chamber other than processing chamber 2C, such as the load lock chamber 1A or 1B or the processing chamber 2A, 2B or 2D. Also, in the present embodiment, the cameras 501a and 501b are disposed in relation to one processing chamber 2, but the cameras 501a and 501b may be respectively disposed in relation to all of the load lock chambers 1A and 1B and the processing chambers 2A to 2D.

The lights 502a and 502b consist of circular lights in which a plurality of light emitting elements are disposed in a ring shape, and a function of the lights 502a and 502b is to illuminate the areas A and B of the substrate S when the areas A and B are captured. The light 502a is disposed in front of the lens of the camera 501a, and the light 502b is disposed in front of the lens of the camera 501b.

The image inspection controller 503 controls the image capture of the areas A and B of the substrate S by the cameras 501a and 501b, and the illumination of the areas A and B of the substrate S by the lights 502a and 502b, and determines whether the substrate S is damaged by pattern matching using the captured images $G_A$ and $G_B$. In the present embodiment, reference images $G_{RA}$ and $G_{RB}$ to be compared with the captured images $G_A$ and $G_B$ by pattern matching are generated from the captured images $G_A$ and $G_B$.

Figure 4:
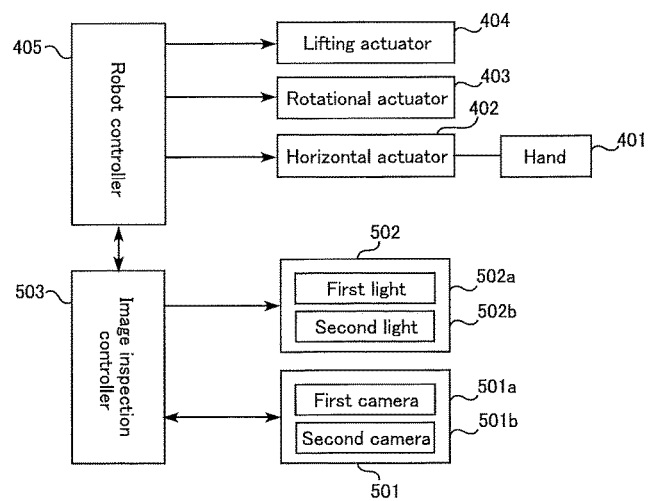
FIG. 4 is a block diagram showing an electrical configuration associated with image detection processing.
Figure 5:
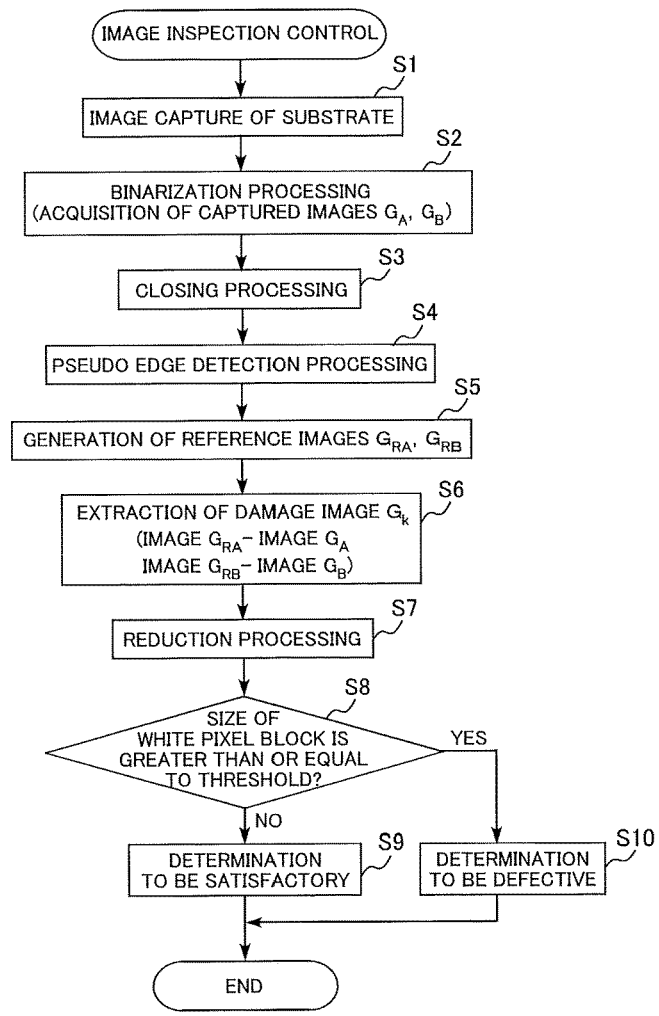
FIG. 5 is a flowchart showing a processing procedure for substrate inspection by the image inspection apparatus.

FIG. 4 is a block diagram showing an electrical configuration that is associated with image detection processing. The camera 501 and the light 502 respectively consolidate cameras 501a and 501b and lights 502a and 502b, and are blocks representing cameras 501a and 501b and lights 502a and 502b.

The robot controller 405 controls the movement of the hand 401 (i.e., setting of the substrate S in the load lock chamber 1 and the processing chamber 2 and removal of the substrate S from the load lock chamber 1 and the processing chamber 2 using the hand 401) by controlling the drive of the lifting actuator 404, the rotational actuator 403, and the horizontal actuator 402. The robot controller 405 has, for example, a microcomputer including a CPU, a ROM, a RAM and an I/O interface that are interconnected as a main constituent element. The robot controller 405 controls the operation for conveying the substrate S with the hand 401, by executing a substrate conveyance program prestored in the ROM.

The image inspection controller 503 controls the image capture operation of the camera 501 and the illumination operation of the light 502, and also controls the inspection of the substrate S by pattern matching using the captured image G ($G_A$, $G_B$) captured with the camera 501. The image inspection controller 503 has, for example, a microcomputer including a CPU, a ROM, a RAM, and an I/O interface that are interconnected as a main constituent element. The image inspection controller 503 controls the processing for determining the quality of the substrate S by executing an image inspection program prestored in the ROM.

As described above, the captured image G is taken by the camera 501 when conveying the substrate S to the processing chamber 2, and thus the robot controller 405 and the image inspection controller 503 are interconnected to enable data communication, in order to control the image capture operation of the camera 501. The image inspection controller 503 controls the image capture operation of the camera 501, based on information on the movement position of the hand 401 that is input from the robot controller 405. Specifically, the image inspection controller 503 controls the start timing and the end timing of image capture by the camera 501.

The operations of the horizontal actuator 402, the rotational actuator 403 and the lifting actuator 404 that are connected to the robot controller 405 and the camera 501 and the light 502 that are connected to the image inspection controller 503 are as described above using FIGS. 1 and 2.

Next, the processing procedure for inspecting the substrate S (determining whether the substrate S is damaged) by the image inspection apparatus 5 will be described using the flowchart of FIG. 5 and FIGS. 6 to 13. Although the case where it is determined whether the edge $E_1$ on the right side of the substrate S is damaged will be described in the following example, the same also applies in the case of determining whether the edge $E_2$ on the left side of the substrate S is damaged.

First, the substrate handling robot 4 starts an operation for extending the hand 401 on which the substrate S is placed and setting the substrate S in the processing chamber 2. The image inspection controller 503 receives input of information on the position of the hand 401 from the robot controller 405. The image inspection controller 503 starts image capture by the camera 501 based on this information, at the timing at which the leading edge $E_3$ of the substrate S enters the field of view of the camera 501. The image inspection controller 503 stops image capture by the camera 501 at the timing at which the trailing edge $E_4$ of the substrate S leaves the field of view of the camera 501. In this way, the images $G_A$ and $G_B$ of the areas A and B of the substrate S are taken by the image inspection controller 503 (S1).

Figure 6A:
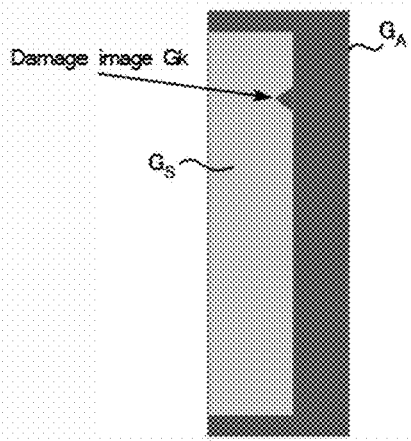
FIGS. 6A and 6B are diagrams for illustrating binarization processing.
Figure 6B:
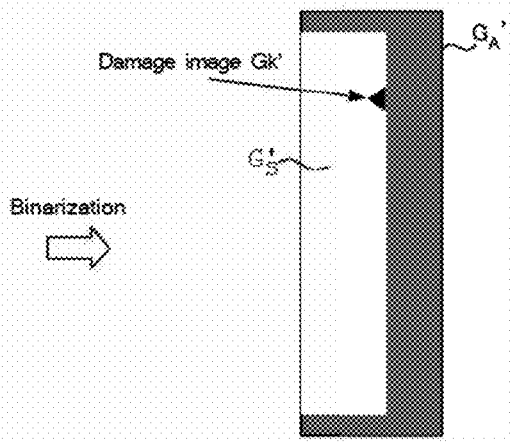

Next, the image inspection controller 503 binarizes the taken images $G_A$ and $G_B$ (S2). For example, the image $G_A$ includes a band-like image $G_S$ (hereinafter, "substrate image $G_S$") of a substrate portion and an image of the remaining portion ("background" or "background portion"), as shown in FIG. 6A. The densities of the substrate portion and the background portion are halftone densities, for example. In the illustrated example, the density of the background portion is greater than the substrate portion. The binarization processing involves allocating one of two predetermined numerical values to each of a large number of pixels $g_i$ (where i is an identification number given to a pixel; i=1, 2, ..., N) constituting the image $G_A$. Specifically, a level $V_i$ ($0 \le V_i \le 1$) of each pixel $g_i$ is compared with a predetermined threshold $V_{th}$ ($0 < V_{th} < 1$), for example. If $V_{th} < V_i$, the level of the pixel $g_i$ is converted to "1" (white level), and if $V_i < V_{th}$, the level of the pixel $g_i$ is converted to "0" (black level). As a result of the binarization processing, the image $G_A$ is converted into an image $G_A'$ (binary image) that includes a white substrate image $G_S'$ on a black background, as shown in FIG. 6B. Similarly, the image $G_B$ is also converted into a binary image $G_B'$.

Then, the image inspection controller 503 performs closing processing on the white pixels of the images $G_A'$ and $G_B'$ ("captured image $G_A'$", "captured image $G_B'$") resulting from the binarization processing (S3). The closing processing involves removing noise (black pixels) and small groups of black pixels included in the substrate image $G_S'$. In the closing processing, reduction processing is performed n times, after performing enlargement processing n times.

Figure 7A:
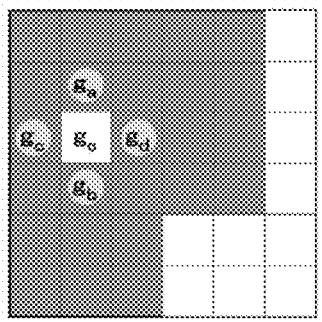
FIGS. 7A and 7B are diagrams for illustrating enlargement processing.
Figure 7B:
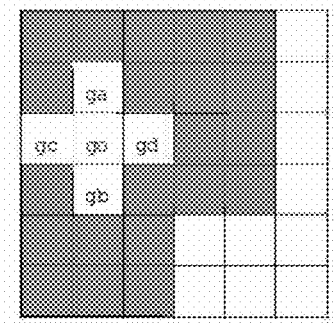
Figure 8A:
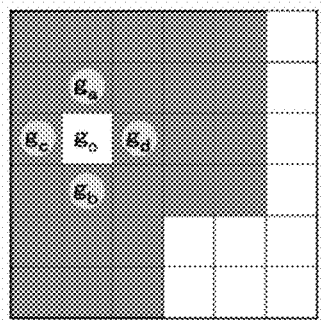
FIGS. 8A and 8B are diagrams for illustrating reduction processing.
Figure 8B:
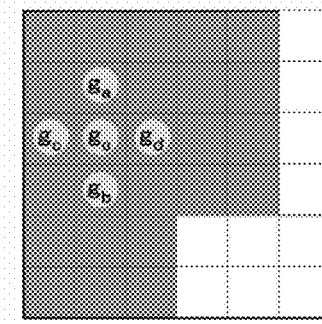

The enlargement processing involves enlarging graphics in the captured image $G_A'$ by one pixel. Accordingly, the enlargement processing on a white pixel involves, for example, converting pixels $g_a$, $g_b$, $g_c$ and $g_d$ that are located above and below and to the left and right of a white pixel $g_o$ to be processed to white pixels, as shown in FIGS. 7A-B. The reduction processing involves reducing graphics in the captured image $G_A'$ by one pixel. The reduction processing is the opposite of enlargement processing, and thus involves the white pixel $g_o$ to be processed being converted to a black pixel the same as the black pixels $g_a$, $g_b$, $g_c$, and $g_d$ that are located above and below and to the left and right, as shown in FIGS. 8A-B.

Figure 9A:
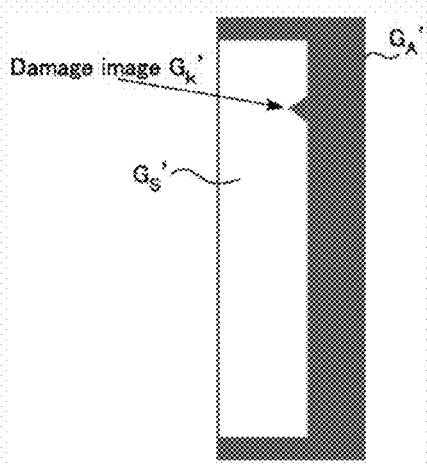
FIGS. 9A and 9B are diagrams for illustrating closing processing.
Figure 9B:
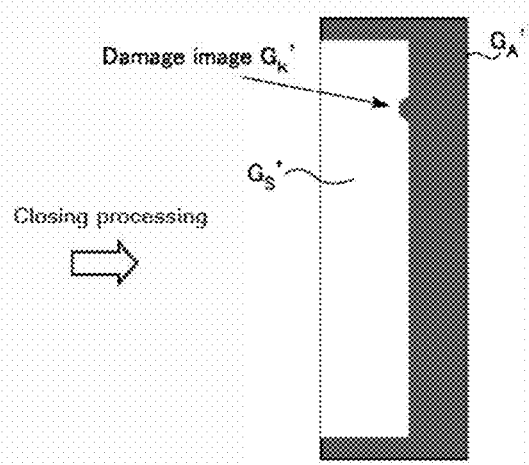

For example, when the closing processing has been performed on the white pixels included in the captured image $G_A'$, the captured image $G_A'$ resulting from the closing processing will be as shown in FIGS. 9A-B. Before the closing processing, an image $G_k'$ of a damaged portion (hereinafter, "damage image $G_k'$") in the substrate image $G_S'$ was triangular in shape, but after the closing processing, the vertex portion of the triangular shape has gone, and the damage image $G_k'$ is trapezoidal in shape.

Then, the image inspection controller 503 performs pseudo edge detection processing on the captured images $G_A'$ and $G_B'$ resulting from the closing processing (S4). For example, in the captured image $G_A'$, the edge portions in the widthwise direction and the edge portion in the lengthwise direction around the substrate image $G_S'$ are respectively equivalent to the edges $E_3$, $E_4$ and $E_1$ of the substrate S (see FIG. 3), and the outline of the substrate image $G_S'$ should consist of straight lines, but sometimes does not consist of straight lines when viewed at a pixel level in the substrate image $G_S'$ included in the captured image $G_A'$ (see FIG. 10A) resulting from the closing processing. Pseudo edge detection processing involves detecting pseudo linear edges $E_3'$, $E_4'$ and $E_1'$ (see FIG. 10E) with respect to the three edge portions of the substrate image $G_S'$.

Figure 10A:
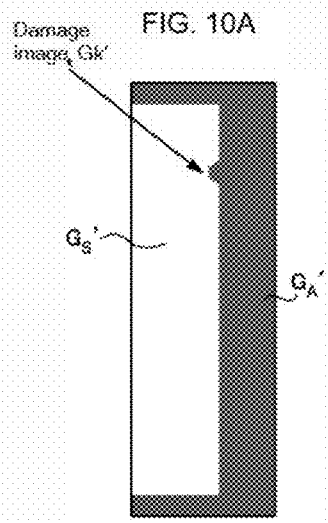
FIGS. 10A-E are diagrams for illustrating pseudo edge detection processing.
Figure 10B:
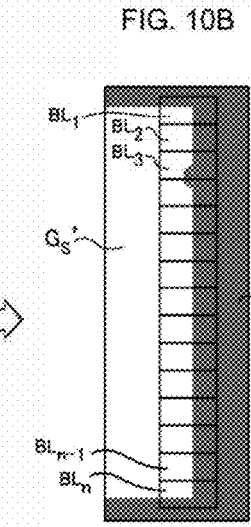
Figure 10C:
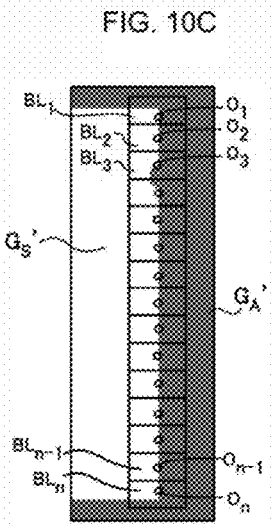

Specifically, the image inspection controller 503, as shown in FIGS. 10B and C, first divides the edge portion (edge portion having damage image $G_k'$) that is equivalent to the edge $E_1$ of the substrate S of the substrate image $G_S'$ into a plurality of blocks $BL_1$, $BL_2$, ..., $BL_n$, and computes a center $O_j$ of the edge portion that is included in each block $BL_j$ (j: number of blocks; j=1, 2, ..., n) in the lengthwise direction. The center $O_j$ is computed by extracting a plurality of pixels $g_E$ constituting the lengthwise edge of the substrate image $G_S'$ that are included in the block $BL_j$, and calculating the average value of the positions of these pixels $g_E$ in the width direction of the substrate image $G_S'$.

Figure 10D:
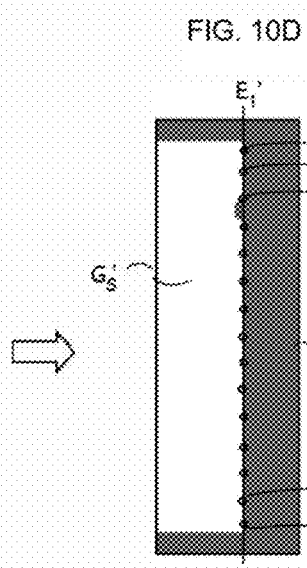
Figure 10E:

The image inspection controller 503 computes a pseudo edge $E_1'$, as shown in FIG. 10D, using the least-squares method on the centers $O_1$, $O_2$, ..., $O_n$ computed for the n blocks $BL_1$, $BL_2$, ..., $BL_n$. Then, the image inspection controller 503 computes a pseudo edge $E_3'$ and a pseudo edge $E_4'$ (see FIG. 10E) with a similar method to the method of calculating the pseudo edge $E_1'$, for the edge portions that are equivalent to the edge $E_3$ and the edge $E_4$ of the substrate S of the substrate image $G_S'$. The image inspection controller 503 also performs similar processing on the captured image $G_B'$ resulting from the closing processing, and computes pseudo edges $E_3'$ and $E_4'$ and a pseudo edge $E_2'$.

When the pseudo edge detection processing has ended, the image inspection controller 503 removes the damage image $G_k'$ and noise by performing processing on the captured images $G_A'$ and $G_B'$ to convert the black pixels of the portion surrounded by the pseudo edges $E_1'$, $E_3'$ and $E_4'$ of the substrate image $G_S'$ to white pixels, as shown in FIGS. 11A-B, and generates a reference image $G_{RA}$ and a reference image $G_{RB}$ (S5). The reference image $G_{RA}$ is an image in which the vertically long rectangular area surrounded by the pseudo edges $E_1'$, $E_3'$ and $E_4$ is constituted by white pixels and the remaining area is constituted by black pixels, with the portion constituted by the white pixels being the substrate image $G_S'$. That is, the reference image $G_{RA}$ is an image in which the substrate image $G_S'$ is a solid white image and the background portion is a solid black image. The reference image $G_{RB}$ is also similarly an image in which the vertically long rectangular area surrounded by the pseudo edges $E_2'$, $E_3'$ and $E_4'$ is constituted by white pixels and the remaining area is constituted by black pixels, with the portion constituted by the white pixels being the substrate image $G_S'$.

Then, the image inspection controller 503, as shown in FIGS. 12A-C, computes a difference $\Delta g_j$ ($=g_j'-g_j$) in levels between pixels $g_j'$ and $g_j$ corresponding to the captured image $G_A'$ and the reference image $G_R$, and generates a difference image $G_{DEF}$ in which the level of each pixel $g_j$ is the difference $\Delta g_j$ (S6). Because the background portions of the reference image $G_{RA}$ and the captured image $G_A'$ are both constituted by black pixels, the level $\Delta g_j$ of each pixel of the background portion will be "0" (black pixel).

On the other hand, the substrate image $G_S'$ of the reference image $G_{RA}$ is constituted by white pixels, although in the case where there is a damaged portion in the substrate image $G_S'$ of the captured image $G_A'$, only the damaged portion is constituted by black pixels and the remaining portion is constituted by white pixels, and thus the area excluding the damaged portion will be "0" (black pixels), and only the area of the damaged portion will be "1" (white pixels). Accordingly, the difference image $G_{DEF}$, in the case where there is a damaged portion, will be an image from which the damage image $G_k'$ has been extracted as a white image. If there is not a damaged portion, the difference image $G_{DEF}$ will be an image from which an image is not extracted as a white image or from which minute images have been extracted as noise.

Then, the image inspection controller 503 performs reduction processing (see FIGS. 8A-B) on the white pixels of the difference image $G_{DEF}$ (see FIG. 13A) for the captured image $G_A'$ and the captured image $G_B'$ (S7), and thereafter extracts white pixels included in the difference image $G_{DEF}$ that form a group (equivalent to damage image $G_k'$ in FIG. 13B) and computes an area $S_k$ of the image thereof. The image inspection controller 503 then compares the computed area $S_k$ with a preset threshold $S_{th}$ (S8), and determines that the substrate S is "good" (S9) if $S_k < S_{th}$ (S8: NO) for both the captured image $G_A'$ and the captured image $G_B'$ and that the substrate S is "defective" (S10) if $S_{th} \leq S_k$ for one or both of the captured image $G_A'$ and the captured image $G_B'$ (S8: YES), and ends the image detection processing.

According to the present embodiment, the reference images $G_{RA}$ and $G_{RB}$ for use in pattern matching are generated from the captured images $G_A$ and $G_B$ that are captured of both the right and left sides of the substrate S when the substrate S is conveyed to the load lock chamber 1 or the processing chamber 2 by the substrate handling robot 4, and thus there is no longer any need to prepare the reference images $G_{RA}$ and $G_{RB}$ in advance, and time and effort for acquiring the reference images $G_{RA}$ and $G_{RB}$ is no longer necessary. Memory for storing reference images $G_{RA}$ and $G_{RB}$ acquired in advance is also no longer necessary.

Also, in a method that involves acquiring the captured images $G_A$ and $G_B$ by moving the camera 501 having a line sensor as the image sensor relative to side portions of the substrate S as a result of the horizontal movement of the substrate S by the substrate handling robot 4, the contents of the captured images $G_A$ and $G_B$ change if there is variation in the movement speed or the movement direction of the moving substrate S, but because the reference images $G_{RA}$ and $G_{RB}$ for use in pattern matching are generated from the captured images $G_A$ and $G_B$ according to the present embodiment, the burden of taking account of variation in the image capture conditions of the substrate S in image inspection is reduced.

In the present embodiment, the fact that the shape of the substrate image $G_S$ is greatly affected by variation in the image capture conditions of the substrate S, and meandering of the edge E of side portions of the substrate image $G_S$ in particular (see FIG. 15C) is a problem, but because the pseudo edges $E_1'$, $E_2'$, $E_3'$ and $E_4'$ that are equivalent to the edges $E_3$ and $E_4$ before and after the substrate S and the edges $E_1$ and $E_2$ of the side portions are detected with respect to the substrate images $G_S$ in the captured images $G_A$ and $G_B$ in the processing procedure for generating the reference images $G_{RA}$ and $G_{RB}$, and the shape of the edge portion of the substrate image $G_S$ is determined using these pseudo edges $E_1'$, $E_2'$, $E_3'$ and $E_4'$, variation in the image capture conditions of the substrate S can be readily handled.

By giving the order of the least-squares method in processing for detecting the pseudo edges $E_1'$ and $E_2'$, meandering of the edge portion of the substrate image $G_S$ due to meandering of the hand 401 can be adequately handled, and the existence of a damage image $G_K'$ can be discriminated with high accuracy.

Although a single-hand substrate handling robot 4 was described in the above embodiment, the present invention is also intended to be applicable in the case of dual-hand substrate handling robots.

Although a configuration that captures the substrate S using the cameras 501a and 501b having a line sensor as the image sensor was described in the above embodiment, an image sensing unit for capturing the substrate S is not limited to this configuration. The image sensing unit may be a camera using an area sensor as the image sensor. Also, the image sensor of the camera may be a color sensor.

Also, although an exemplary configuration in which the cameras 501a and 501b are installed at entrance portions of the load lock chamber 1 or the processing chamber 2 was described in the above embodiment, a configuration may be adopted in which a camera is provided on the substrate handling robot 4, and a peripheral portion of the substrate S is captured with the camera in a state where the substrate S is placed on the hand 401.

In the above embodiment, the captured images $G_A'$ and $G_B'$ resulting from binarization were images in which the background portion was a black image and the substrate portion was a white image, but may be images in which the background portion is a white image and the substrate portion is a black image.

In the above embodiment, processing is performed to convert the black pixels of the portion surrounded by the pseudo edge $E_1'$, $E_3'$ and $E_4'$ of the captured images $G_A'$ and $G_B'$ to white pixels, after performing the pseudo edge detection processing subsequent to the closing processing, and the captured images $G_A'$ and $G_B'$ are changed to solid images. However, a configuration may be adopted in which the reference images $G_{RA}$ and $G_{RB}$ are generated after performing only the closing processing in the case where the damaged portion is small.

Although an example in the case where a side portion of the substrate S is missing was described as exemplary damage to the substrate S, the present invention can also be applied in the case where the side portion of the substrate S is cracked. Also, although a rectangular substrate S was described as an example in the above embodiment, the shape of the substrate S is not limited to a rectangle. For example, because a captured image that includes an elongated substrate image $G_S$ can be acquired by moving a camera having a line sensor relatively along the periphery of the substrate S even in the case of a circular substrate S, the quality of the substrate S can be determined by the abovementioned image detection method.

Although the substrate S of the substrate processing system X was described as the inspection target in the above embodiment, the present invention can be widely applied to image inspection for inspecting the quality of an inspection target by pattern matching through comparison of a captured image that is captured of the inspection target with a reference image.

The invention claimed is:

1. An image inspection apparatus that determines a recessed damaged portion at an edge of an inspection substrate, comprising:
   an image sensing unit that acquires a captured image including a first image portion of the inspection substrate having the edge; the image sensing unit includes a camera, the camera having a field of view that covers at least a portion of the inspection substrate, and the camera is positioned such that the edge of the inspection substrate and a portion of the inspection substrate recessed from the edge are included within the field of view;
   an image inspection controller communicatively connected to the image sensing unit to control operation of the camera and to receive data from the image sensing unit, the image inspection controller includes:
      a reference image generation unit that generates a reference image that includes a second image portion of the inspection substrate, by performing image processing on the first image portion of the captured image, the image processing comprises changing a shape of the portion of the inspection substrate recessed from the edge; and
      a determination unit that generates a difference image by taking a difference between the reference image and the captured image, the difference image includes a damage image, and the determination unit determines a quality of the inspection substrate based on the damage image,
   wherein the damage image indicates the recessed damaged portion at the edge of the inspection substrate in a plan view of the inspection substrate.

2. The image inspection apparatus according to claim 1, wherein the image processing that is performed by the reference image generation unit includes closing processing on the first image portion of the captured image.

3. The image inspection apparatus according to claim 1, wherein the inspection substrate is rectangular, and has two side portions spaced from each other, one of the side portions includes the edge and the other one of the side portions includes a second edge, and the inspection substrate is conveyed by a handling robot, the image sensing unit includes a second camera, the second camera having a field of view that covers at least a portion of the inspection substrate, and the second camera is positioned such that the second edge of the inspection substrate is included within the field of view of the second camera, and each of the cameras has a line sensor extending in a direction orthogonal to a conveyance direction of the inspection substrate by the handling robot, and takes an image of one of the two side portions of the inspection substrate by performing an image capture operation during a period in which the line sensor and the one side portion of the inspection substrate move relative to each other as a result of the inspection substrate being conveyed by the handling robot.

4. The image inspection apparatus according to claim 2, wherein the inspection substrate is rectangular, and has two side portions spaced from each other, one of the side portions includes the edge and the other one of the side portions includes a second edge, and the inspection substrate is conveyed by a handling robot, the image sensing unit includes a second camera, the second camera having a field of view that covers at least a portion of the inspection substrate, and the second camera is positioned such that the second edge of the inspection substrate is included within the field of view of the second camera, and each of the cameras has a line sensor extending in a direction orthogonal to a conveyance direction of the inspection substrate by the handling robot, and takes an image of one of the two side portions of the inspection substrate by performing an image capture operation during a period in which the line sensor and the one side portion of the inspection substrate move relative to each other as a result of the inspection substrate being conveyed by the handling robot.

5. The image inspection apparatus according to claim 4, wherein the reference image generation unit, after performing the closing processing, further detects a pseudo edge that is equivalent to an outline of the inspection substrate in the captured image, and generates the reference image based on an image area surrounded by the pseudo edge.

6. The image inspection apparatus according to claim 1, wherein the determination unit performs reduction processing on the damage image, and, in a case where an area of an image resulting from the reduction processing is greater than or equal to a preset threshold, determines that the inspection substrate is defective.

7. The image inspection apparatus according to claim 1, wherein the image sensing unit includes at least one light.

8. The image inspection apparatus according to claim 1, wherein the reference image generation unit removes the damage image from the first image portion of the captured image so that the damage image does not appear in the reference image.

9. An image inspection method for determining a recessed damaged portion at an edge of an inspection substrate, comprising:

acquiring a captured image of the inspection substrate with an image sensing unit, the captured image including a first image portion of the inspection substrate;

generating a reference image that includes a second image portion of the inspection substrate, by performing image processing on the first image portion of the captured image, the image processing comprises changing a shape of the recessed damaged portion; and generating a difference image by taking a difference between the reference image and the captured image, the difference image includes a damage image, and determining a quality of the inspection substrate based on the damage image, wherein the damage image indicates the recessed damaged portion at the edge of the inspection substrate in a plan view of the inspection substrate.

10. The image inspection method according to claim 9, wherein the inspection substrate is rectangular, has two side portions spaced from each other, and is conveyed by a handling robot, the image sensing unit includes two cameras that capture the two side portions of the inspection substrate, each of the cameras has a line sensor extending in a direction orthogonal to a conveyance direction of the inspection substrate by the handling robot, in acquiring the captured image of the inspection substrate, an image of one of the two side portions of the inspection substrate is taken by performing an image capture operation during a period in which the line sensor moves relative to the one side portion of the inspection substrate as a result of the inspection substrate being conveyed by the handling robot, and in generating the reference image, the reference image is generated by performing closing processing on an image of the inspection substrate that is included in the image taken with each camera.

11. The image inspection method according to claim 9, wherein generating the reference image includes removing the damage image from the first image portion of the captured image so that the damage image does not appear in the reference image.

* * * * *